US008026384B2

(12) United States Patent
Finnhult et al.

(10) Patent No.: US 8,026,384 B2
(45) Date of Patent: Sep. 27, 2011

(54) PROCESS FOR THE SYNTHESIS OF ALKYL PHOSPHINIC ACIDS BY INITIATION OF AN AMINE AND AN AMINEOXIDE

(75) Inventors: Daniel Finnhult, Sodertalje (SE); Roger Sohlberg, Sodertalje (SE); Fredrik Stalfors, Sodertalje (SE); Carina Svensson, Sodertalje (SE); Johanna Wachtmeister, Sodertalje (SE); Thomas Wannman, Sodertalje (SE)

(73) Assignee: AstraZeneca AB, Sodertalje (SE)

( * ) Notice: Subject to any disclaimer, the term of this patent is extended or adjusted under 35 U.S.C. 154(b) by 141 days.

(21) Appl. No.: 12/598,782

(22) PCT Filed: Apr. 30, 2008

(86) PCT No.: PCT/SE2008/050496
§ 371 (c)(1),
(2), (4) Date: Nov. 4, 2009

(87) PCT Pub. No.: WO2008/136746
PCT Pub. Date: Nov. 13, 2008

(65) Prior Publication Data
US 2010/0130773 A1    May 27, 2010

Related U.S. Application Data

(60) Provisional application No. 60/915,979, filed on May 4, 2007.

(51) Int. Cl.
*C07C 269/06* (2006.01)
(52) U.S. Cl. .................. 560/160; 560/161
(58) Field of Classification Search .................. 560/160, 560/161
See application file for complete search history.

(56) References Cited

U.S. PATENT DOCUMENTS

| 2,724,718 | A | 11/1955 | Stiles et al. |
| 4,632,741 | A | 12/1986 | Wolf et al. |
| 6,576,626 | B2 | 6/2003 | Elebring et al. |
| 7,034,176 | B2 | 4/2006 | Elebring et al. |
| 2003/0130253 | A1 | 7/2003 | Dorwald et al. |
| 2003/0191112 | A1 | 10/2003 | Dorwald |

FOREIGN PATENT DOCUMENTS

| EP | 1055676 | 8/2003 |
| EP | 0343307 | 6/2007 |
| WO | 0141743 | 6/2001 |
| WO | 0142252 | 6/2001 |
| WO | 03024929 | 3/2003 |
| WO | 2004037800 | 5/2004 |
| WO | 2004054973 | 7/2004 |
| WO | 2005028438 | 3/2005 |
| WO | 2006038870 | 4/2006 |

OTHER PUBLICATIONS

An et al., "Synthesis of novel 3'-C-methylene thymidine and 5-methyluridine/cytidine H-phosphonates and phosphonamidites for new backbone modification of oligonucleotides.," J Org Chem (2001) 66(8):2789-2801.
Issleib et al., "Bis(trimethylsilyl)-hypophosphit und Alkoxycarbonylphosphonigsäure-bis(trimethylsilyl)ester als Schlüsubstanzen für die Synthese von Organophosphorverbindungen," Zeitshrift fur Anorganische und Allegmeine Chemie (1985) 530(11):16-28.
Livanstove et al., "Synthesis and properties of aloxy(trimethylsiloxy)phosphines and their derivatives," J General Chemistry of the USSR (1985) pp. 1976-1985.
Alstermark et al., "Synthesis and pharmacological evaluation of novel gamma-aminobutyric acid type B (GABAB) receptor agonists as gastroesophageal reflux inhibitors," J Med Chem (2008) 51(14):4315-4320.
Froestl et al., "Phosphinic acid analogues of GABA. 1. New potent and selective GABAB agonists.," J Med Chem (1995) 38(17):3297-3312.
Deprele et al., "Triethylborane-initiated room temperature radical addition of hypophosphites to olefins: synthesis of monosubstituted phosphinic acids and esters," J Org Chem (2001) 66(20):6745-6755.
International-Type Search Report, Issued in priority Swedish Application 0401971-7 on Feb. 25, 2005.
International Search Report, Issued in corresponding PCT/SE2005/001189 on Oct. 6, 2005.
Official Action dated Apr. 30, 2009 received in co pending U.S. Appl. No. 11/572,967.
Simonsson et al., "Synthesis of 14C-labeled AZD-3355," Synthesis and Applications of Isotopically Labelled Compounds (2004) 8:33-36.
Rosenau et al., "Radicals derived from N-methylmorpholine-N-oxide (NMMO): structure, trapping and recombination reactions," Tetrahedron (2002) 58(15):3073-3078.
Winqvist et al., "Reactions of 3-C-Halomethyl and 3-C-Sulfonylmethyl Uridines with Phosphinic Acid Derivatives—Synthesis of Building Blocks for Oligonucleotides Containing 3-C-Methylenephosphonate Linkages," Eur. J. Org. Chem. (2002) 2002(9):1509-1515.

*Primary Examiner* — Peter O Sullivan
(74) *Attorney, Agent, or Firm* — Pepper Hamilton LLP

(57) ABSTRACT

The present invention relates to a new process for the synthesis of alkyl phosphinic acids, and more particularly to a coupling reaction between an alkylhalide and a hypophosphorous acid derivative in the presence of an amine and an amineoxide.

11 Claims, No Drawings

PROCESS FOR THE SYNTHESIS OF ALKYL PHOSPHINIC ACIDS BY INITIATION OF AN AMINE AND AN AMINEOXIDE

FIELD OF THE INVENTION

The present invention relates to a new process for the synthesis of alkyl phosphinic acids from alkyl halides.

BACKGROUND OF THE INVENTION

Reactions between an alkyl halide and the hypophosphorous acid derivative, bis(trimethylsilyl)hypophosphite, is previously known from K. Issleib et al., Z. anorg. Chem. 530 (1985), pp. 16-28.

A radical initiated reaction between a hypophosphorous acid and an alkene is disclosed in Deprèle, S., et al., J. Org. Chem., 2001, 66, 6745-6755. The reaction is a radical addition of hypophosphites to olefins and the radical reaction is initiated by trialkylboranes and oxygen.

Winqvist A., et al., Eur. J. Org. Chem., 2002, 1509-1515, describe, inter alia, synthesis of phosphinic acids from alkyl halides and bis(trimethylsilyl)hypophosphite. The publication describes the influence of the temperature during the reaction.

WO 01/41743 discloses (aminopropyl)methylphosphinic acids and the synthesis thereof starting from protected aminopropylhalides and a hypophosphorous acid derivative.

U.S. Pat. No. 2,724,718 and U.S. Pat. No. 4,632,741 disclose the synthesis of phosphinate salts through a radical addition of a hypophosphite salt to olefins by means of irradiation with UV light in the presence of a photoinitiator.

EP 1055676 discloses a process for the preparation of dialkylphosphinic acids by free radical-initiated reaction with olefins.

Many initiators in the collection of suitable radical initiators require heat addition for initiating the reaction. Also oxygen can be used as an initiator for a radical reaction. However, some of the hypophosphorous acid derivatives are pyrophoric and therefore oxygen is not a suitable initiator in large-scale production. One such example is the hypophosphorous acid derivative bis(trimethylsilyl)hypophosphite.

Chemical radical initiators would be possible for initiating the reaction between an alkyl halide and a hypophosphorous acid derivative. Most often, when such initiators are used, the reaction is started by raising the temperature of the reaction mixture. However, temperature is also a critical parameter for reduction of the amount of by-products, the lower temperature the lower amount of by-products. The disadvantage of lowering the temperature is that also the reaction rate is reduced at a low temperature, and this has implications for the result and the yield of the desired product. Therefore, there is a need for a process where the amount of by-products obtained are kept low in parallel with a fast and efficient reaction rate.

WO 2006/038870 discloses that UV-light can catalyze the reaction between alkyl iodides and BTHP in the formation of alkyl phosphinic acids. The use of UV-light is convenient on lab-scale, but it has proven to be difficult to find viable technical solutions on larger scales.

Outline of the Invention

The present invention relates to a new process for the synthesis of alkyl phosphinic acids starting from alkyl halides and a hypophosphorous acid derivative in the presence of an amine and an aminoxide.

More particularly, the present invention relates to a process for the synthesis of a compound of formula I

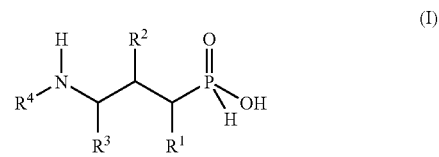

(I)

wherein
$R^1$ is selected from hydrogen; $C_1$-$C_{10}$-alkyl; $C_1$-$C_{10}$-alkoxy; fluorine; and chlorine;
$R^2$ is selected from hydroxy; fluorine; chlorine; oxo; and $C_1$-$C_{10}$-alkoxy;
$R^3$ is selected from hydrogen and $C_1$-$C_6$-alkyl;
$R^4$ is selected from hydrogen and $C(O)R^5$;
$R^5$ is selected from $C_1$-$C_{10}$ alkyl and $C_1$-$C_{10}$ alkoxy;
comprising reacting a compound of formula II

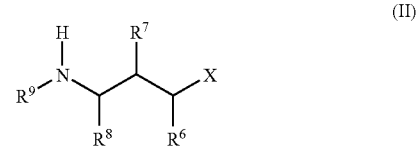

(II)

$R^6$ is selected from hydrogen; $C_1$-$C_{10}$-alkyl; $C_1$-$C_{10}$-alkoxy; fluorine; and chlorine;
$R^7$ is selected from hydroxy; fluorine; chlorine; oxo; and $C_1$-$C_{10}$-alkoxy;
$R^8$ is selected from hydrogen and $C_1$-$C_6$-alkyl;
$R^9$ is selected from hydrogen and $C(O)R^{10}$;
$R^{10}$ is selected from $C_1$-$C_{10}$ alkyl and $C_1$-$C_{10}$ alkoxy; and
X is iodide or bromide;
with a compound of formula III

(III)

wherein
to $R^{11}$ and $R^{12}$ are each and independently selected from $C_1$-$C_{10}$ alkyl and $Si(R^{13})_3$;
and
$R^{13}$ is a $C_1$-$C_6$ alkyl;
in the presence of an amine and an aminoxide.

When the substituent $R^2$ and/or $R^7$ is oxo, then this substituent is bound to the carbon atom by a double bond. In this case, no hydrogen atom is bound to said carbon atom.

In another embodiment, the compound of formula II is prepared by reacting another compound of formula II, wherein X is mesyloxy, with one or more halides.

In another embodiment, the halides are selected from sodium iodide and tetrabutylammonium iodide.

In another embodiment, the compound of formula I is

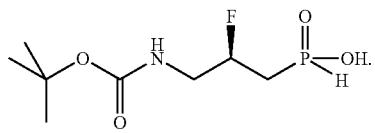

In another embodiment, the compound of formula II is

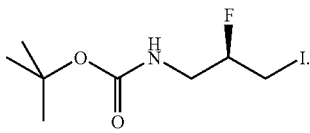

In another embodiment, the compound of formula III is bis(trimethylsilyl)hypophosphite.

In another embodiment, the amine is selected from hexamethyldisilazan, N-methylmorpholine, trimethylamine, triethylamine, diisopropylethylamine, and 2,2,6,6-tetramethylpiperidine.

In another embodiment, the amineoxide is selected from trimethylamineoxide, N-methylmorpholineoxide (NMM-oxide) and 2,2,6,6-tetramethylpiperidineoxy radical (TEMPO).

In another embodiment, the reaction is performed in the presence of toluene, tetrahydrofuran, acetonitrile, ethyl acetate or in a mixture thereof.

In another embodiment, the reaction is performed at a temperature of from −70° C. to 20° C.

In another embodiment, the reaction is performed at a temperature of from −70° C. to 0° C.

As used herein:
ACN refers to acetonitrile;
BTHP refers to bis(trimethylsilyl)hypophosphite;
DIPEA refers to diisopropyl ethyl amine;
EtOAc refers to ethyl acetate;
HPLC refers to high performance liquid chromatography;
IPC refers to in-process control;
MEK refers to methyl ethyl ketone;
NMM refers to N-methylmorpholine;
PEG refers to polyethylene glycol;
QI refers to tetrabutylammonium iodide;
TEMPO refers to 2,2,6,6-tetramethylpiperidineoxy radical;
THF refers to tetrahydrofuran;
TLC refers to thin layer chromatography.

According to the present invention, NMM is used in the reaction mentioned above as a base forming a precipitate with the hydrogen iodide generated in the reaction. NMM-oxide is used as a catalyst. Process development based on these findings resulted in a method that gives reproducible results on 1000-L scale, resulting in a shorter reaction time and a slightly higher yield.

Unless otherwise stated the term "$C_1$-$C_{10}$ alkyl" as used throughout this specification includes linear or branched $C_1$-$C_{10}$ alkyl. Examples of $C_1$-$C_{10}$ alkyl include, but are not limited to, $C_1$-$C_6$ alkyl such as methyl, ethyl, propyl, n-propyl, isopropyl, butyl, iso-butyl, sec-butyl, tert-butyl, pentyl and hexyl.

Unless otherwise stated, the term "alkoxy" denotes an O-alkyl, wherein alkyl is as defined above. The term "$C_1$-$C_{10}$ alkoxy" as used throughout this specification includes linear or branched $C_1$-$C_{10}$ alkoxy. Examples of $C_1$-$C_{10}$ alkoxy include, but are not limited to, $C_1$-$C_6$ alkoxy such as methoxy, ethoxy, propoxy, n-propoxy, and tert-butoxy.

The synthesis of the phosphinic acids according to the present invention can be performed at temperatures at or below approximately room temperature, i.e. at a temperature of or below 20° C. The effect of lowering the temperature is that the various side reactions and the amount of by-products limiting the yield of the reaction can be reduced. According to one embodiment of the invention, the reaction mixture is held at a temperature of approximately 0° C. By lowering the reaction temperature to approximately −70° C. an increased yield can be achieved. Dehalogenation is a side reaction, which occurs. However, the dehalogenation is suppressed by lowering the temperature, and thus, the production of the sideproducts is suppressed.

An alkyl phosphinic acid is produced according to the present invention by adding the alkyl halide dissolved in a solvent which may be organic to a cooled solution comprising the hypophosphorous acid derivative in an inert environment, i.e. an environment free from oxygen attained by using nitrogen or argon.

The components for forming the hypophosphorous acid derivative, i.e. the hypophosphite to group, are, for example, ammonium hypophosphite and hexamethyldisilazan, ammonium hypophosphite, DIPEA and trimethylsilyl chloride. They are mixed in a vessel until the reaction is completed, the reaction mixture is then cooled and kept in an environment free from oxygen.

For example, when BTHP is being used as the hypophosphorous acid derivative, the first step of the synthesis for obtaining alkylphosphinic acids is the formation of BTHP. The formation of the hypophosphorous acid derivative just before the addition of the alkyl halide is an advantage since the hypophosphorous acid derivative is highly pyrophoric. The alkyl halide is then added and the reaction is thereafter initiated by NMM and NMM-oxide. The completion of the reaction is measured by, for example, HPLC or TLC.

During the process of the invention, a neutralisation of the hydrogen halide formed during the reaction can be performed by having a base present during the synthesis of the phosphinic acid. The base is suitably an amine such as hexamethyldisilazan, N-methylmorpholine, trimethylamine, triethylamine, or DIPEA.

The reaction is conducted in an aprotic organic solvent, for example, toluene, THF, EtOAc, acetonitrile, MEK, or in a mixture thereof.

The compound formed is recovered by extraction in a polar solvent such as ethyl acetate, isopropanol, n-butanol or a mixture thereof.

By mixture thereof is meant a mixture of two or more of said solvents.

The compounds synthesised according to the claimed process of the present invention can form salts with bases. Salts with bases are, for example, alkali metal salts, e.g. sodium or potassium salts, or those with ammonia or organic amines.

The process according to the present invention is an efficient as well as an economical process for the preparation of alkylphosphinic acids. The following Examples will further illustrate the invention, but are not intended to limit the scope of the invention as described herein or as claimed below.

EXAMPLES

Large-Scale Process for Synthesizing (2R)-3-[(tert-butoxycarbonyl)amino]-2-fluoropropylphosphinate ammonium salt (Compound 2)

The compound in question was synthesized in the following way:

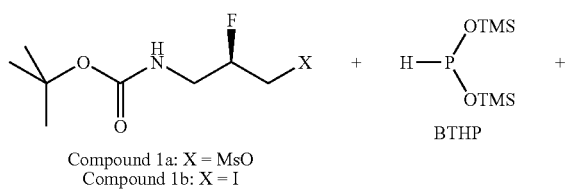

Compound 1a: X = MsO
Compound 1b: X = I

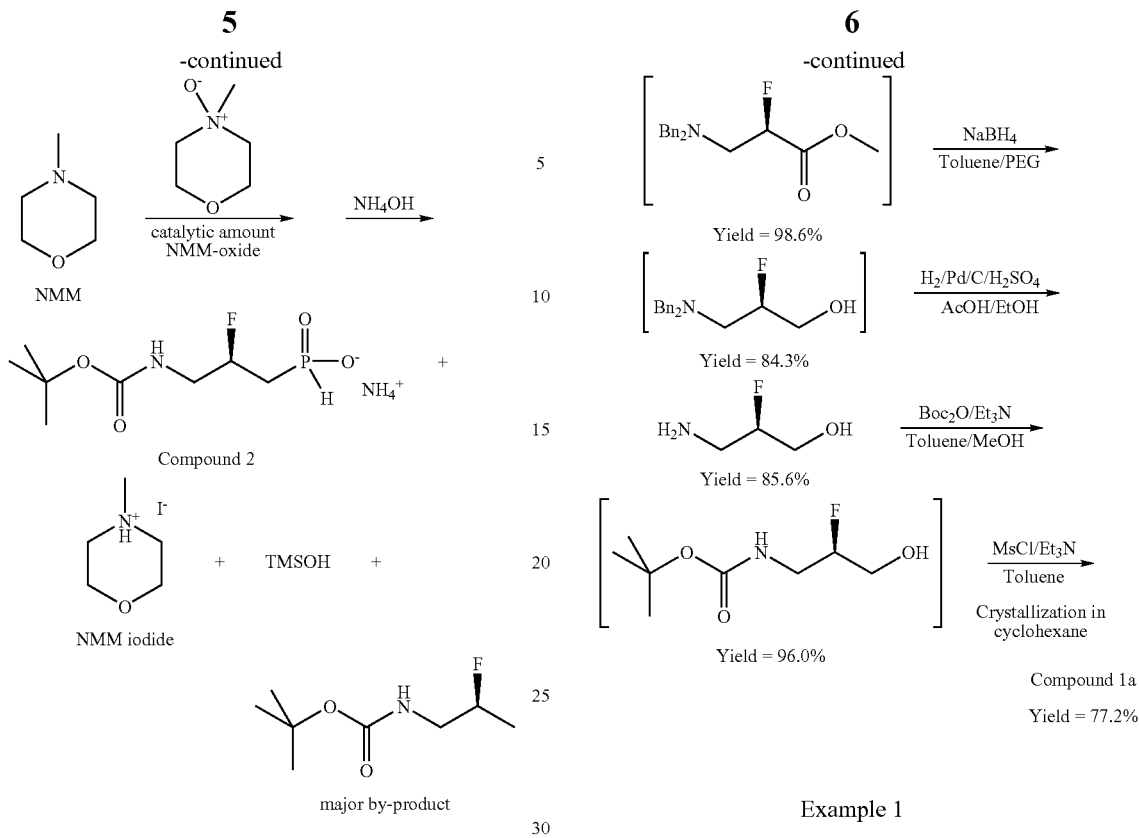

As a starting material, either tert-butyl (2R)-2-fluoro-3-mesyloxypropyl carbamate (Compound 1a) or tert-butyl (2R)-2-fluoro-3-iodopropyl carbamate (Compound 1b) was used. If Compound 1a is used as a starting material, it must first be converted into Compound 1b (Example 1). The preparation of Compound 1b is also disclosed in Example 19 of WO 01/41743.

The synthesis of the Compound 2 starting from Compound 1b and BTHP has been disclosed in Example 7 of WO 2006/038870.

Compound 1a may be synthesized as follows (overall yield 52%):

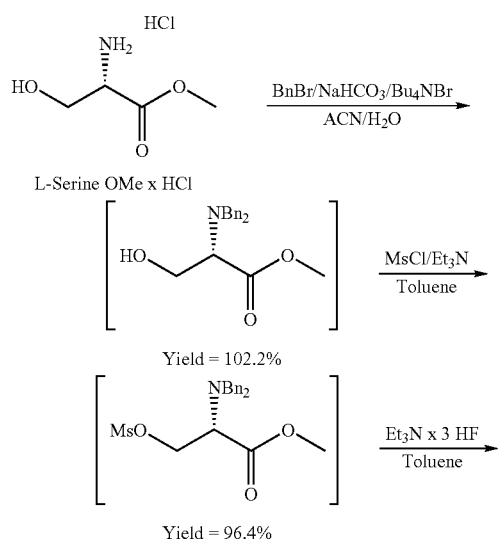

Example 1

Conversion of Compound 1a into Compound 1b (NaI)

Compound 1a (1.0 eq, 80 kg), sodium iodide (NaI, 2.0 eq, 88.4 kg) and methyl ethyl ketone (MEK, 8 vol, 640 L) are charged and the formed slurry is stirred at 60° C. At complete reaction (~20 h) the slurry is cooled to 20° C. and water (1.4 vol, 112 L) is added to dissolve the precipitate. The phases are allowed to separate and the water phase is discarded. Subsequently, a solution of $Na_2SO_3$ (0.33 eq, 11.9 kg) in water (1.3 vol, 100 L) is added to reduce the formed iodine to iodide, which produces a discolored organic phase. The phases are separated and the water phase is discarded. The organic phase is concentrated under reduced pressure to approximately 25% of the total volume. Toluene (6.5 vol, 520 L) is added and the concentration under reduced pressure is repeated to approximately 50% of the total volume. Water (0.6 vol, 48 L) is charged to the solution to the dissolve the salts that may have precipitated during the concentration. The phases are separated and the water phase is discarded. Toluene (2.2 vol, 176 L) is charged and the remaining solution is concentrated to approximately 65% of the total volume. The solution of Compound 1b in toluene is charged as is to the solution of BTHP (below). Typical yield on 1000-L scale=90%. Assay ~30% w/w.

Example 2

Synthesis of Compound 2 Starting from Compound 1b (toluene-acetonitrile)

Ammonium hypophosphite (2.0 eq, 43.1 kg) is allowed to react with hexamethyldisilazane (4.0 eq, 167.5 kg) in toluene (2 vol, 156 L) at 100° C. during 8-10 hours under inert atmosphere forming BTHP. Compound 1b (from Example 1) dissolved in toluene (2.3 vol, 179 L) is charged to the BTHP-solution at −10° C. followed by controlled additions of NMM-oxide (0.01 eq, 301 g) dissolved in acetonitrile (0.13 vol, 10 L) and then NMM (1.0 eq, 26.0 kg). The mixture is allowed to react until the IPC shows complete conversion of the starting material (normally 1 hour). The reaction mixture is quenched by the addition of ammonium hydroxide 25% w/w (4.0 eq, 70.0 kg) and water (3.0 vol, 236 L). The obtained phases are separated and the organic layer is discarded. The mixture is made acidic (pH~4.5) by addition of 4.5 M sulphuric acid (~1.2 eq, 67.7 L) and an aqueous solution of ammonium sulphate (4.1 eq, 140.0 kg, 2.7 vol, 208 L) is charged. The solution is extracted twice with n-butanol (2×4.1 vol, 319 L). The combined n-butanol layers are basified by addition of ammonium hydroxide 25% w/w (0.5 eq, 8.7 kg) and partially concentrated (to half the volume). Acetonitrile (4.2 vol, 327 L) is charged slowly at 65° C., whereupon the product precipitates. The obtained Compound 2 is isolated by filtration, washed with acetonitrile (4.2 vol, 327 L) and dried at 40° C. Typical yield on 1000-L scale=53-57%. (yield from Compound 1a=50-53%) Assay 90-93% w/w.

$^1$H NMR (D$_2$O, δ in ppm) 6.97 (m, 1H, $^1J_{PH}$=512 Hz, H—P), 4.80 (m, 1H, $^2J_{HF}$=43.4 Hz, H-2), 3.30 (m, 1H, H-3a), 3.20 (m, 1H, H-3b), 1.96 (m, 1H, H-1a), 1.68 (m, 1H, H-1b), 1.31 (s, 9H, t-Bu).

Example 3

Synthesis of Compound 2 Starting from Compound 1a (THF-acetonitrile)

Compound 1a (1.0 eq, 100 kg), sodium iodide (NaI, 1.5 eq, 82.9 kg) and tetrahydrofuran (THF, 6.0 vol, 600 L) are charged and the mixture is allowed to react at 65-68° C. At complete reaction (~24 h) the slurry is cooled to 0° C. and salts are filtered off. The precipitation is washed with THF (2 vol, 200 L). The filtrate is concentrated to approximately 3 volumes relative weight of Compound 1a. The solution of Compound 1b in THF is charged as is to the solution of BTHP (below). Ammonium hypophosphite (1.5 eq, 45.9 kg) is allowed to react with hexamethyldisilazane (3.0 eq, 178.5 kg) in THF (1.5 vol, 150 L) at 68° C. during 15 hours under inert atmosphere forming BTHP.

Compound 1b (from above) dissolved in THF (3 vol, 300 L) is charged to the BTHP-solution at −10° C. followed by controlled additions of NMM-oxide (0.05 eq, 2.2 kg) dissolved in acetonitrile (0.2 vol, 20 L) and then NMM (1.0 eq, 37.3 kg). The mixture is allowed to react until the IPC shows complete conversion of the starting material (normally 0.5 hour). The reaction mixture is quenched by the addition of ammonium hydroxide 25% w/w (1.0 eq, 25.1 kg) and water (2.0 vol, 200 L). The obtained phases are separated and the organic layer is discarded. The mixture is made acidic (pH~4.5) by addition of 4.5 M sulphuric acid (~0.4 eq, 32.7 L) and an aqueous solution of ammonium sulphate (2.5 eq, 122 kg, 2.0 vol, 200 L) is charged. The solution is extracted twice with n-butanol (2×4.0 vol, 400 L). The combined n-butanol layers are basified by addition of ammonium hydroxide 25% w/w (1 eq, 25.1 kg) and partially concentrated to 4 volumes relative weight of Compound 1a. Acetonitrile (4.0 vol, 400 L) is charged slowly at 65° C., whereupon the product precipitates. The obtained Compound 2 is isolated by filtration, washed with acetonitrile (4.0 vol, 400 L) and dried at 40° C. Typical yield on 1000-L scale from Compound 1a=44-47%. Assay 85-87% w/w.

Example 4

Synthesis of Compound 2 Starting from Compound 1a (toluene-OI)

Compound 1a (1.0 eq, 600 g), sodium iodide (NaI, 1.5 eq, 497 g), tetrabutylammonium iodide (QI, 0.2 eq, 163 g) and toluene (6.0 vol, 3600 mL) are charged and the mixture is allowed to react at 65-68° C. At complete reaction (~24 h) the slurry is cooled to 20° C. and water (2.0 vol, 1200 mL) is added. The phases are separated and the organic layer is concentrated to approximately 3 volumes relative weight of Compound 1a. The solution of Compound 1b in toluene is charged as is to the solution of BTHP (below). Ammonium hypophosphite (1.5 eq, 275 g) is allowed to react with hexamethyldisilazane (3.0 eq, 1071 g) in toluene (1.5 vol, 900 mL) at 100° C. during 12 hours under inert atmosphere forming BTHP.

Compound 1b (from above) dissolved in toluene (3 vol, 1800 mL) is charged to the BTHP-solution at −10° C. followed by controlled additions of NMM-oxide (0.05 eq, 13 g) dissolved in acetonitrile (0.2 vol, 120 mL) and then NMM (1.0 eq, 224 g). The mixture is allowed to react until the IPC shows complete conversion of the starting material (normally 0.5 hour). The reaction mixture is quenched by the addition of ammonium hydroxide 25% w/w (1.0 eq, 151 g) and water (2.0 vol, 120 mL). The obtained phases are separated and the organic layer is discarded. The mixture is made acidic (pH~4.5) by addition of 4.5 M sulphuric acid (~0.4 eq, 196 mL) and an aqueous solution of ammonium sulphate (2.5 eq, 731 g, 2.0 vol, 1200 mL) is charged. The solution is extracted twice with n-butanol (2×4.0 vol, 2400 mL). The combined n-butanol layers are basified by addition of ammonium hydroxide 25% w/w (1 eq, 151 g) and partially concentrated to 4 volumes relative weight of Compound 1a. Acetonitrile (4.0 vol, 2400 mL) is charged slowly at 65° C., whereupon the product precipitates. The obtained Compound 2 is isolated by filtration, washed with acetonitrile (4.0 vol, 2400 mL) and dried at 40° C. Typical yield on 5-L scale from Compound 1a=48%. Assay 86% w/w.

Example 5

Synthesis of Compound 2 Starting from Compound 1a (EtOAc-toluene)

Compound 1a (1.0 eq, 600 g), sodium iodide (NaI, 1.5 eq, 497 g) and EtOAc (4.0 vol, 2400 mL) are charged and the mixture is allowed to react at 65-68° C. At complete reaction (~24 h) the slurry is cooled to 20° C. and water (1.5 vol, 900 mL) and toluene (2.0 vol, 1200 mL) are added. The phases are separated and the organic layer is concentrated to approximately 3 volumes relative weight of Compound 1a. The solution of Compound 1b in EtOAc/toluene is charged as is to the solution of BTHP (below). Ammonium hypophosphite (1.5 eq, 275 g) is allowed to react with hexamethyldisilazane (3.0 eq, 1071 g) in toluene (1.5 vol, 900 mL) at 100° C. during 12 hours under inert atmosphere forming BTHP.

Compound 1b (from above) dissolved in toluene (3 vol, 1800 mL) is charged to the BTHP-solution at −10° C. followed by controlled additions of NMM-oxide (0.05 eq, 13 g) dissolved in acetonitrile (0.2 vol, 120 mL) and then NMM (1.0 eq, 224 g). The mixture is allowed to react until the IPC shows complete conversion of the starting material (normally 0.5 hour). The reaction mixture is quenched by the addition of ammonium hydroxide 25% w/w (1.0 eq, 151 g) and water (2.0 vol, 120 mL). The obtained phases are separated and the organic layer is discarded. The mixture is made acidic (pH~4.5) by addition of 4.5 M sulphuric acid (~0.4 eq, 196 mL) and an aqueous solution of ammonium sulphate (2.5 eq, 731 g, 2.0 vol, 1200 mL) is charged. The solution is extracted twice with n-butanol (2×4.0 vol, 2400 mL). The combined n-butanol layers are basified by addition of ammonium hydroxide 25% w/w (1 eq, 151 g) and partially concentrated to 4 volumes relative weight of Compound 1a. Acetonitrile (4.0 vol, 2400 mL) is charged slowly at 65° C., whereupon the product precipitates. The obtained Compound 2 is isolated by filtration, washed with acetonitrile (4.0 vol, 2400 mL) and dried at 40° C. Typical yield on 5-L scale from Compound 1a=48%. Assay 95% w/w.

The invention claimed is:

1. A process for the synthesis of a compound of formula I

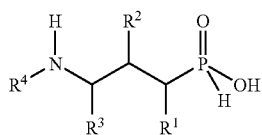
(I)

wherein
- $R^1$ is selected from hydrogen; $C_1$-$C_{10}$-alkyl; $C_1$-$C_{10}$-alkoxy; fluorine; and chlorine;
- $R^2$ is selected from hydroxy; fluorine; chlorine; oxo; and $C_1$-$C_{10}$-alkoxy;
- $R^3$ is selected from hydrogen and $C_1$-$C_6$-alkyl;
- $R^4$ is selected from hydrogen and $C(O)R^5$;
- $R^5$ is selected from $C_1$-$C_{10}$ alkyl and $C_1$-$C_{10}$ alkoxy;

comprising reacting a compound of formula II

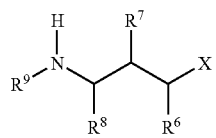
(II)

wherein
- $R^6$ is selected from hydrogen; $C_1$-$C_{10}$-alkyl; $C_1$-$C_{10}$-alkoxy; fluorine; and chlorine;
- $R^7$ is selected from hydroxy; fluorine; chlorine; oxo; and $C_1$-$C_{10}$-alkoxy;
- $R^8$ is selected from hydrogen and $C_1$-$C_6$-alkyl;
- $R^9$ is selected from hydrogen and $C(O)R^{10}$;
- $R^{10}$ is selected from $C_1$-$C_{10}$ alkyl and $C_1$-$C_{10}$ alkoxy; and
- X is iodide or bromide;

with a compound of formula III

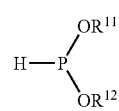
(III)

wherein
- $R^{11}$ and $R^{12}$ are each and independently selected from $C_1$-$C_{10}$ alkyl and $Si(R^{13})_3$; and
- $R^{13}$ is a $C_1$-$C_6$ alkyl;

in the presence of an amine and an aminoxide.

2. A process according to claim 1, wherein the compound of formula II is prepared by reacting another compound of formula II, wherein X is mesyloxy, with one or more halides.

3. A process according to claim 2, wherein the halides are selected from sodium iodide and tetrabutylammonium iodide.

4. A process according to claim 1, wherein the compound of formula I is

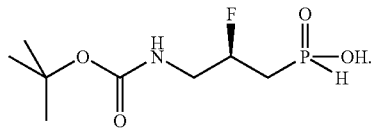

5. A process according to claim 1 wherein the compound of formula II is

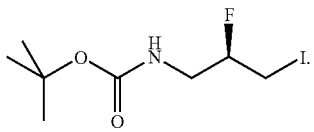

6. A process according to claim 1, wherein the compound of formula III is bis(trimethylsilyl)hypophosphite.

7. A process according to claim 1, wherein the amine is selected from hexamethyldisilazan, N-methylmorpholine, trimethylamine, triethylamine, diisopropylethylamine, and 2,2,6,6-tetramethylpiperidine.

8. A process according to claim 1, wherein the aminoxide is selected from trimethylaminoxide, N-methylmorpholin-eoxide and 2,2,6,6tetramethylpiperidineoxy radical.

9. A process according to claim 1, wherein the reaction is performed in the presence of toluene, tetrahydrofuran, acetonitrile, ethyl acetate or in a mixture thereof.

10. A process according to claim 1, whereby the reaction is performed at a temperature of from −70° C. to 20° C.

11. A process according to claim 10, whereby the reaction is performed at a temperature of from −70° C. to 0° C.

* * * * *